United States Patent [19]

Janssen

[11] Patent Number: 5,475,182
[45] Date of Patent: Dec. 12, 1995

[54] ACID EXTRACTION OF MOLECULAR SIEVE CATALYSTS TO IMPROVE ETHYLENE YIELD

[75] Inventor: Marcel J. G. Janssen, Houston, Tex.

[73] Assignee: Exxon Chemical Patents Inc., Houston, Tex.

[21] Appl. No.: 98,567

[22] Filed: Jul. 27, 1993

Related U.S. Application Data

[63] Continuation of Ser. No. 889,540, May 27, 1992, abandoned.

[51] Int. Cl.⁶ .................................................. C07C 1/00
[52] U.S. Cl. ........................ 585/640; 585/638; 585/639; 502/79; 502/64; 502/214
[58] Field of Search ...................... 585/638, 639, 585/640; 502/79, 64, 214

[56]  References Cited

U.S. PATENT DOCUMENTS

| | | |
|---|---|---|
| 2,378,236 | 6/1945 | Miller . |
| 3,928,483 | 12/1975 | Chang et al. . |
| 4,025,575 | 5/1977 | Chang et al. . |
| 4,440,871 | 4/1984 | Lok et al. . |
| 4,486,617 | 12/1984 | Hoelderich et al. . |
| 4,496,786 | 1/1985 | Santilli et al. . |
| 4,499,327 | 2/1985 | Kaiser . |
| 4,503,281 | 3/1985 | Hoelderich et al. . |
| 4,579,993 | 4/1986 | Bowes et al. . |
| 4,602,119 | 7/1986 | Drake . |
| 4,617,283 | 10/1986 | Coughlin ................... 502/214 |
| 4,677,242 | 6/1987 | Kaiser ...................... 585/640 |
| 4,677,243 | 6/1987 | Kaiser . |
| 4,724,270 | 2/1988 | Chang et al. . |
| 4,814,541 | 3/1989 | Lewis . |
| 4,849,575 | 7/1989 | Lewis ...................... 585/640 |
| 4,861,938 | 8/1989 | Lewis et al. . |
| 4,867,954 | 9/1989 | Staniulis et al. . |
| 4,873,390 | 10/1989 | Lewis et al. . |
| 4,874,590 | 10/1989 | Staniulis et al. . |
| 4,973,792 | 11/1990 | Lewis et al. . |
| 5,013,536 | 5/1991 | Vaughn et al. . |
| 5,126,308 | 6/1992 | Barger et al. ............. 502/208 |

FOREIGN PATENT DOCUMENTS

| | | |
|---|---|---|
| 0022640 | 1/1980 | European Pat. Off. . |
| 0105512 | 4/1984 | European Pat. Off. . |

Primary Examiner—Anthony McFarlane
Assistant Examiner—E. D. Irzinski
Attorney, Agent, or Firm—Linda K. Russell

[57] ABSTRACT

A method for enhancing ethylene yield in the conversion of oxygenates to olefins that involves extracting molecular sieve catalysts, such as silicoaluminophosphate catalysts, with a mineral acid is provided. Acid extraction is thought to alter the crystallinity of the molecular sieve catalyst and thereby improve ethylene yield.

20 Claims, No Drawings

ACID EXTRACTION OF MOLECULAR SIEVE CATALYSTS TO IMPROVE ETHYLENE YIELD

CROSS REFERENCE TO RELATED APPLICATION

This is a continuation of application Ser. No. 07/899,540 filed May 27, 1992 and now abandoned.

BACKGROUND OF THE INVENTION

This invention relates to a process for enhancing ethylene yield in microporous solid catalysts used in the conversion of oxygenates to hydrocarbons or olefins. More particularly, this invention relates to a process for enhancing ethylene yields using silicoaluminophosphate molecular sieve catalysts through acid extraction of the catalysts.

Light olefins have traditionally been produced through the process of petroleum cracking. Because of the limited availability and high cost of petroleum sources, the cost of producing light olefins from such petroleum sources has been steadily increasing. Many raise the dire prediction of significant oil shortages in the not-too-distant future. Curtailment in the availability of inexpensive petroleum raw materials threatens the supply of light olefins. Light olefins serve as feeds for the production of numerous chemicals. Ethylene is a light olefin used as a feedstock in many chemical processes.

The search for alternative materials for the production of light olefins or ethylene has led to the use of oxygenates such as alcohols, and more particularly to methanol and ethanol or their derivatives as feedstocks. These and other alcohols may be produced by fermentation or from synthesis gas. Synthesis gas can be produced from natural gas, petroleum liquids, carbonaceous materials including coal, recycled plastics, municipal wastes, or any organic material. Thus, alcohol and alcohol derivatives may provide non-petroleum based routes for hydrocarbon production.

Molecular sieves, such as the crystalline zeolite and silicoaluminophosphate (SAPO) catalysts, are known to promote the conversion of oxygenates to hydrocarbon mixtures. Numerous patents describe this process for various types of molecular sieve catalysts: U.S. Pat. Nos. 3,928,483; 4,025,575; 4,252,479 (Chang, et al.); 4,496,786 (Santilly, et al.); 4,677,243 (Kaiser). However, none of these patents teach or suggest that ethylene yield may be enhanced through treatment of the catalyst with acid.

These and other disadvantages of the prior art are overcome by the present invention, however, and a new improved process for enhancing ethylene yield through the acid treatment of catalysts is provided.

SUMMARY OF THE INVENTION

In accordance with the present invention, a process for improving ethylene yield in the conversion of oxygenates to hydrocarbons is provided. The process involves acid extraction of a molecular sieve catalyst such as a silicoaluminophosphate (SAPO), and more particularly, SAPO-34. Acid extraction with mineral acids alters the crystallinity of the molecular sieve and enhances ethylene yield.

It is an object of the present invention to provide a method for improving ethylene yields in the conversion of oxygenates to olefins, comprising, extracting a molecular sieve catalyst with an acid, then converting an oxygenate to olefins with the acid-extracted molecular sieve catalyst to provide olefins with improved ethylene yields.

This and other advantages of the present invention will become apparent from the following detailed description.

DETAILED DESCRIPTION OF THE INVENTION

The present invention relates to a method for enhancing ethylene yield in the conversion of oxygenates to olefins comprising extracting a molecular sieve catalyst with an acid, then converting an oxygenate feed to olefins with the acid-extracted molecular sieve catalyst to provide olefins with improved ethylene yields. Any of the large number of molecular sieve catalysts, such as, but not limited to, the zeolite catalysts, can be used in the present invention. Ethylene yield is enhanced by treating the molecular sieve catalyst with an acid. More specifically, this invention employs acid extraction of SAPO catalysts to improve ethylene yields.

SAPO catalysts exhibit properties of both aluminosilicate zeolites and aluminophosphates. The SAPO's have a three-dimensional microporous crystal framework structure of $PO_2^+$, $AlO_2^{31}$ and $SiO_2$ tetrahedral units. The chemical composition (anhydrous) is:

mR: $(Si_xAl_yP_z)O_2$ wherein "R" represents at least one organic templating agent present in the intracrystalline pore system: "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular SAPO species involved, and "x", "y" and "z" represent the mole fractions of silicon, aluminum and phosphorus, respectively.

The process for producing ethylene employs a feedstock comprising "oxygenates." The term oxygenates as employed herein comprises hydrocarbons containing aliphatic moieties such as, but not limited to, alcohols, halides, mercaptans, sulfides, amines, ethers and carbonyl compounds (aldehydes, ketones, carboxylic acids and the like) or mixtures thereof. The aliphatic moiety preferably contains from about 1 to about 10 carbon atoms and more preferably contains about 1 to about 4 carbon atoms. Representative oxygenates include, but are not limited to, lower straight or branched chain alcohols, their unsaturated counterparts and the nitrogen, halogen and sulfur analogues of such. Examples of suitable compounds include, but are not limited to, methanol; isopropanol; n-propanol; ethanol; fuel alcohols; methyl mercaptan; methyl sulfide; methyl amine; dimethyl ether; ethyl mercaptan; ethyl chloride; diethyl ether; methylethyl ether; formaldehyde; dimethyl ketone; acetic acid; n-alkyl amines; n-alkyl halides and n-alkyl sulfides having n-alkyl groups of 3 to 10 carbon atoms; and mixtures thereof. The term "oxygenate feed" as employed in the present invention and described herein designates only the organic material used as the feed. The total charge of feed to the reaction zone may contain additional compounds such as diluents.

The ethylene production process is preferably carried out in the vapor phase such that the feedstock is contacted in a vapor phase in a reaction zone with a molecular sieve at effective process conditions so as to produce the desired light olefins, i.e., an effective temperature, pressure, WHSV (Weight Hourly Space Velocity) and, optionally, an effective amount of diluent, correlated to produce light olefins. Alternatively, the process may be carried out in a liquid phase. When the process is carried out in the liquid phase the process necessarily involves the separation of products formed in a liquid reaction media and can result in different conversions and selectivities of feedstock-to-product with respect to the relative ratios of the light olefin products as compared to that formed by the vapor phase process.

The temperature which may be employed in the process may vary over a wide range depending, at least in part, on the selected molecular sieve catalyst. In general, the process can be conducted at an effective temperature between about 200° C. (392° F.) and about 700° C. (1292° F.), preferably between about 250° C. (482° F.) and about 600° C. (1112° F.), and most preferably between about 300° C. (572° F.) and about 500° C. (932° F.). Temperatures outside the stated range are not excluded, although they do not fall within certain desirable embodiments of the present invention. At the lower end of the temperature range, and thus, generally, at a lower rate of reaction, the formation of the desired light olefin products may become markedly slow. At the upper end of the temperature range and beyond, the process may not form an optimum amount of light olefin products. Notwithstanding these factors, the reaction will still occur and the feedstock, at least in part, can be converted to the desired light olefin products at temperatures outside the range between about 200° C. (392° F.) and about 700° C. (1292° F.).

The process is effectively carried out over a wide range of pressures including autogeneous pressures. At pressures between about 0.001 atmospheres (0.76 torr) and about 1000 atmospheres (760,000 torr), the formation of light olefin products will be effected although the optimum amount of product will not necessarily form at all pressures. The preferred pressure is between about 0.01 atmospheres (7.6 torr) and about 100 atmospheres (76,000 torr). The pressures referred to herein for the process are exclusive of the inert diluent, if any, that is present, and refer to the partial pressure of the feedstock as it relates to oxygenate compounds and/or mixtures thereof. Pressures outside the stated range are not excluded from the scope of this invention, although such do not fall within certain desirable embodiments of the invention. At the lower and upper end of the pressure range, and beyond, the selectivities, conversions and/or rates to light olefin products may not occur at the optimum, although light olefins such as ethylene may still be formed.

The process is effected for a period of time sufficient to produce the desired light olefin products. In general, the residence time employed to produce the desired product can vary from seconds to a number of hours. It will be readily appreciated that the residence time will be determined to a significant extent by the reaction temperature, the molecular sieve selected, the WHSV, the phase (liquid or vapor), and the process design characteristics selected.

The process is effectively carried out over a wide range of WHSV for the feedstock and is generally between about 0.01 hr.$^{-1}$ and about 100 hr.$^{-1}$ and preferably between about 0.1 hr.$^{-1}$ and about 40 hr.$^{-1}$. Values above 100 hr.$^{-1}$ may be employed and are intended to be covered by the instant process, although such are not presently preferred.

The olefin production process is generally carried out in the presence of one or more inert diluents which may be present in the feedstock in an amount between about 1 and about 99 molar percent, based on the total number of moles of all feed and diluent components fed to the reaction zone (or catalyst). Typical of diluents which may be employed in the instant process are helium, argon, nitrogen, carbon monoxide, carbon dioxide, hydrogen, water, paraffins, hydrocarbons (such as methane and the like), aromatic compounds, mixtures thereof and the like. The preferred diluents are presently believed to comprise mixtures of water and aromatic diluents.

The olefin production process may be carried out in a batch, semi-continuous or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of such SAPO molecular sieves in series to provide for a desired product mixture. Owing to the nature of the process, it may be desirous to carry out the process of the present invention by use of the molecular sieve catalysts in a dynamic (e.g. fluidized or moving) bed system or any system of a variety of transport beds rather than in a fixed bed system. Such systems would readily provide for any regeneration (if required) of the molecular sieve catalyst after a given period of time. If regeneration is required, the molecular sieve catalyst can be continuously introduced as a moving bed to a regeneration zone where it can be regenerated, such as for example by removing carbonaceous materials or by oxidation in an oxygen-containing atmosphere. In the preferred practice of the invention, the catalyst will be subject to a regeneration step by burning of carbonaceous deposits accumulated during reactions.

It is well known that the catalytic and adsorptive properties of the molecular sieve catalyst may be varied by changing the ions within the catalyst. Appropriate materials that can be used in this ion-exchange process are ammonia and various acids, including hydrochloric acid, having a low molar strength. The use of acids during ion-exchange does not significantly alter the X-ray diffraction pattern, the inflection of the X-ray peaks or the crystallinity of the molecular sieve.

The present invention employs the extraction of molecular sieve catalysts with acids to increase olefin yields and, more particularly, to increase ethylene yields. The present invention teaches a method for improving ethylene yields in the conversion of oxygenates to olefins, comprising extracting a molecular sieve catalyst with an acid, then converting an oxygenate feed to olefins with the acid-extracted molecular sieve catalyst to improve ethylene yields. The molecular sieve catalyst may be a SAPO catalyst, such as, but not limited to, SAPO-34, or a zeolite catalyst.

This acid treatment of the catalysts may alter the X-ray diffraction pattern of the catalyst, the inflection of the X-ray peaks and the crystallinity of the molecular sieve. Although the exact mechanism whereby acid treatment improves ethylene yield is not known, it is thought to be related to changes in the crystallinity of the molecular sieve catalyst.

Representative acids that can be used include, but are not limited to, hydrochloric, hydrofluoric, sulfuric, phosphoric and acetic acids or any mineral acids or mixtures thereof. Acid strength may be from about 0.1N to about 1N, preferably about 0.01N to about 0.1N and more preferably about 0.001N to about 0.01N. Extraction times with the acid may be varied from about 0 hours to about 100 hours, preferably from about 0 hours to about 30 hours, and more preferably from about 23 to about 26 hours. After acquiring knowledge of the teachings of the present invention, those skilled in the art will be able to select the appropriate acid, acid strength and extraction time to improve olefin or ethylene yield.

The following example serves to illustrate specific embodiments of the process of this invention but should not be considered as a limitation on the scope of the invention.

EXAMPLE

SAPO-34 was prepared as described in U.S. Pat. No. 4,440,871. SAPO-34 was extracted at room temperature for 24 hours with separately each of the following: water, 0.01N, 0.005N, or 0.001N HCl. After extraction, the solid was washed, dried, and calcined at 500° C. (932° F.).

Crystallinity was determined using a standard X-ray powder diffraction technique. The radiation source was a high intensity, copper target X-ray tube operated at 40 Kv and 40 ma. The diffraction pattern from the copper K$\alpha$ radiation was recorded by an X-ray spectrometer scintillation counter, pulse height analyzer and strip chart recorder. Flat compressed powder samples were scanned at 2$\Theta$ (2 theta) per minute using a two second time constant. Interplanar spacings (d) in Angstrom units were obtained from the position of the diffraction peaks expressed as 2$\Theta$ where $\Theta$ is the Bragg angle as observed on the strip chart. Intensities were determined from the heights of diffraction peaks after subtracting background, "$I_o$" being the intensity of the strongest line or peak and "I" being the intensity of each of the other peaks. The d-spacings used herein were 44.137–1.343 Angstroms. The reference sample (the SAPO-34 not acid-treated) was arbitrarily set at 100% crystallinity.

The catalytic conversion of methanol/water (1/4 molar ratio) to olefins such as ethylene was carried out in a fixed bed ½" diameter (1.27 cm), stainless steel reactor, equipped with a ⅛" (0.32 cm) coiled preheater. In addition, the reactor was equipped with a ⅛" (0.32 cm) thermocouple well running axially through the reactor. The reactor was inserted into and heated in an Applied Test Systems 3 zone tube furnace (12", 30.5 cm long; 1¼", 3.18 cm I.D.) having one reactor with three spaced "zones." The first reactor zone was used as a preheater zone; the catalyst bed was heated in the second reactor zone. The third reactor zone operates as a quench zone maintained at a temperature of about 200° C. (392° F.) to about 300° C. (572° F.).

Generally, 2 grams (0.07 ounces) of catalyst (−14/+20 mesh) were mixed with 2.5 grams (0.09 ounces) of quartz (−20/+60 mesh); the first and third zones of the reactor were filled with quartz chips (−10/+20 mesh). To improve the heat transfer between the second reactor zone (containing the catalyst bed) and the furnace heating coils, the second reactor zone was equipped with a cylindrical (~4", 10.2 cm long; 1¼", 3.18 cm O.D.) aluminum or stainless steel block. This block contained a central hole in order to be able to measure the block temperature.

Gas flows (nitrogen or hydrogen) were controlled by mass flow controllers, while liquid feed rates were controlled by a Beckmann 114M pump or a Sage 341B syringe pump.

The product emerging from the reactor was analyzed on line for ethylene with a Porepack Q column using a thermal conductivity detector. The reaction was conducted at a WHSV= 1.0 hr.$^{-1}$. The reaction was conducted at 450° C. (842° F.). The results are shown in the Table.

Table

| Treatment | Crystallinity | Ethylene yield (wt %, excluding H$_2$O) |
|---|---|---|
| Water | 100 | 32 |
| 0.01 N HCl | 28 | 42 |
| 0.005 N HCl | 10 | 41 |
| 0.001 N HCl | 12 | 43 |

Thus, in the conversion of oxygenates to olefins, ethylene yield was improved by the extraction of the molecular sieve with acid.

Many other variations and modifications may be made in the techniques hereinbefore described, by those having experience in this technology, without departing from the concept of the present invention. Accordingly, it should be clearly understood that the methods described in the foregoing description are illustrative only and are not intended as a limitation on the scope of the invention.

What is claimed is:

1. A method for converting oxygenates to olefins, comprising extracting a silicoaluminophosphate (SAPO) catalyst with an acid which is from about 0.0001N to about 1N in strength to produce an acid extracted catalyst, then treating an oxygenate feed with said acid extracted catalyst under effective conversion conditions to form an olefin product.

2. A method according to claim 1, wherein said silicoaluminophosphate is SAPO-34.

3. A method according to claim 1, wherein said acid is a mineral acid.

4. A method according to claim 3, wherein said acid is selected from the group consisting of hydrochloric, hydrofluoric, acetic, phosphoric and sulfuric acids, or mixtures thereof.

5. A method according to claim 4, wherein said acid is hydrochloric acid.

6. A method according to claim 1, wherein said acid is about 0.001N to about 0.01N in strength.

7. A method according to claim 1, wherein aid extracting is conducted for up to about 100 hours.

8. A method according to claim 7, wherein said extracting is conducted for up to about 30 hours.

9. A method according to claim 1, wherein said method for converting an oxygenate feed to olefins using said acid-extracted silicoaluminophosphate (SAPO) is conducted at a temperature of from about 200° C. (392° F.) to about 700° C. (1292° F.).

10. A method according to claim 9, wherein said method for converting an oxygenate feed to olefins is conducted at a temperature of from about 250° C. (482° F.) to about 600° C. (1112° F.).

11. A method according to claim 10, wherein said process for converting an oxygenate feed to olefins is conducted at a temperature from about 300° C. (572° F.) to about 500° C. (932° F.).

12. A method according to claim 1, wherein said oxygenate feed is selected from the group consisting of methanol, dimethyl ether, diethyl ether, isopropanol, n-propanol, ethanol, or mixtures thereof.

13. A method according to claim 12, wherein said oxygenate feed is methanol.

14. A method according to claim 1, wherein said oxygenate feed also includes a diluent.

15. A method according to claim 14, wherein said diluent is selected from the group consisting of water, nitrogen gas (N$_2$), hydrogen gas (H$_2$), paraffins, olefins, and aromatics, or mixtures thereof.

16. A method according to claim 15, wherein said diluent is water.

17. A method according to claim 8, wherein said extracting is conducted for about 23 to about 26 hours.

18. A method for converting oxygenates to olefins, comprising treating an oxygenate feed with an acid-extracted silicoaluminophosphate (SAPO) catalyst wherein said silicoaluminophosphate is SAPO-34, wherein said catalyst has been extracted with an acid which is from about 0.0001N to about 1N in strength, wherein said acid is hydrochloric acid, and wherein said extraction step is conducted for up to about 30 hours under effective conversion conditions to form an olefin product.

19. A method according to claim 18, wherein said method for converting an oxygenate feed to olefins is conducted at a temperature of from about 250° C. (482° F.) to about 600° C. (1112° F.) and wherein said oxygenate feed comprises methanol.

20. A method according to claim 1 wherein said oxygenate feed is a fuel alcohol.

* * * * *